US005981527A

United States Patent [19]
Daugan et al.

[11] Patent Number: 5,981,527
[45] Date of Patent: Nov. 9, 1999

[54] CYCLIC GMP-SPECIFIC PHOSPHODIESTERASE INHIBITORS

[75] Inventors: Alain Claude-Marie Daugan; Francoise Gellibert, both of Les Ulis, France

[73] Assignee: ICOS Corporation, Bothell, Wash.

[21] Appl. No.: 09/000,192

[22] PCT Filed: Jul. 11, 1996

[86] PCT No.: PCT/EP96/03025

§ 371 Date: May 15, 1998

§ 102(e) Date: May 15, 1998

[87] PCT Pub. No.: WO97/03985

PCT Pub. Date: Feb. 6, 1997

[30] Foreign Application Priority Data

Jul. 14, 1995 [GB] United Kingdom ............... 9514465

[51] Int. Cl.$^6$ ................. C07D 471/14; A61K 31/395
[52] U.S. Cl. ............................. 514/250; 544/343
[58] Field of Search ..................... 514/250; 544/343

[56] References Cited

U.S. PATENT DOCUMENTS

| 3,644,384 | 2/1972 | Schulenberg | 260/295 C |
| 3,717,638 | 2/1973 | Schulenberg | 260/268 PC |
| 3,917,599 | 11/1975 | Saxena et al. | 260/268 PC |
| 4,188,390 | 2/1980 | Campbell | 424/251 |
| 4,686,228 | 8/1987 | Campbell et al. | 514/307 |
| 5,145,852 | 9/1992 | Virag | 514/253 |
| 5,270,323 | 12/1993 | Milne, Jr. et al. | 514/309 |

FOREIGN PATENT DOCUMENTS

| 0 357 122 | 3/1990 | European Pat. Off. | C07D 471/04 |
| 0 362 555 | 4/1990 | European Pat. Off. | C07D 241/08 |
| 459 666 | 12/1991 | European Pat. Off. | A61K 31/505 |
| 463 756 | 1/1992 | European Pat. Off. | C07D 487/04 |
| 526 004 | 2/1993 | European Pat. Off. | C07D 487/04 |
| 03044324 | 2/1991 | Japan | A61K 31/52 |
| 1 454 171 | 10/1976 | United Kingdom | C07D 471/14 |
| 1454171 | 10/1976 | United Kingdom | C07D 471/14 |
| WO 89/10123 | 11/1989 | WIPO | A61K 31/35 |
| WO 94/05661 | 3/1994 | WIPO | C07D 471/04 |
| WO 94/28902 | 12/1994 | WIPO | A61K 31/505 |
| WO 95/19978 | 7/1995 | WIPO | C07D 471/14 |

OTHER PUBLICATIONS

E. McMahon et al., *J. Pharmacol. Exp. Thera.*, (1989), 251, 1000–1005.
F. Holmquist et al., *Acta Physiol. Scand.*, (1991), 143, 299–304.
G. Barbanti, *Urol. Res.*, (1988), 16, 299–302.
L. Ignarro et al., *Biochem. and Biophys. Res. Comm.*, (1990), 170(2), 843–850.
J. Krall et al., *Bio. Reprod.*, (1988), 39, 913–922.
M. Wilkins et al., *Proc. Natl. Acad. Sci., USA*, (1990, Aug.), 87, 6465–6469.
M. Wilkins et al., *J. Clin. Invest.*, (1990, Apr.), 85, 1274–1279.

J. Rajfer, *N. Eng. J. Med.*, (1992, Jan.), 326(2), 90–94.
H. Knispel, *Urol. Res.*, (1992), 20, 253–257.
G. Gwinup, *Annals. of Internal Medicine*, (1988, Jul.), 162–163.
A. Zorgniotti, *J. Urol.*, (1992, Apr.), 147(4), 308A.
K. Azadozoi et al., *J. Urol.*, (1992, Nov.), 148, 1587–1591.
K. Azadozoi et al., *J. Urol.*, (1992, Jan.), 147, 220–225.
C. Sparwasser et al., *J. Urol.*, (1994, Dec.), 152, 2159–2163.
T. Lue, "Campbell's Urology," 6th Ed., Chap. 16, P. Walsh et al., Eds., W.B. Saunders Co., 709–728 (1991).
N. Kim et al., *J. Clin. Invest.*, (1991), 88, 112–118.
S. Francis et al., in J. Beavo et al. eds. "Cyclic Nucleotide PDEs," Ch. 5 (1990) 117–140.
R. Weishaar et al., *J. Med. Chem.*, (1985), 28:5, 537–542.
H. Ahn et al., *Biochem. Pharmacol.*, (1989), 39:19, 3331–3339.
C. Lugnier et al., *Biochem. Pharmacol.*, (1986), 35:10, 1743–1751.
J. Doremieux et al., *Ann. Urol. Paris*, (1987), 21(6), 429–434.
D. Green et al., *Geriatics*, (1993, Jan.), 48(1), 46–58.

(List continued on next page.)

*Primary Examiner*—Mukund J. Shah
*Assistant Examiner*—Deepak Rao
*Attorney, Agent, or Firm*—Marshall, O'Toole, Gerstein, Murray & Borun

[57] ABSTRACT

A compound having the formula (I)

(I)

and solvates thereof, wherein:

$R^0$ represents hydrogen, halogen or $C_{1-6}$ alkyl;

$R^1$ represents hydrogen or $C_{1-6}$alkyl;

$R^2$ represents the bicyclic ring which may be optionally substituted by one or more groups selected from halogen and $C_{1-3}$alkyl; and $R^3$ represents hydrogen or $C_{1-3}$alkyl is disclosed.

The compounds are potent and selective inhibitors of cGMP-specific PDE, and are useful in a variety of therapeutic areas where such inhibition is beneficial.

13 Claims, No Drawings

OTHER PUBLICATIONS

M. Webster et al., *Hematol. Oncol. Cl. of N. Am.,* (1990, Feb.), 4(1), 265–289.
F. Holmquist et al., *Acta. Physiol. Scand.,* (1991), 141, 441–442.
J. Taher et al., *J. Urol.,* (1993, Apr.), 149, 285A.
S. Uckert et al., *J. Urology.,* 151(5 Suppl), p. 495A (1994).
W. Aronson et al., *J. Urol.,* (1991), 145 (4 Supp.), 341A.
P. Bush et al., *Fed. Am. Soc. Exp. Biol.,* (1991), 5(4), 175.
P. Bush et al., *Fed. Am. Soc. Exp. Biol.,* (1992), 6(4), 2092.
W. Aronson et al., *J. Urol.,* (1992), 147 (4 Supp.), 454A.
P. Bush et al., *Circulation,* (1993, May), 87 Supp. V, V–30–V–32.
R. Pickard et al., *J. Urol.,* (1993, May) 149 (4 Supp.), 245A.
R. Pickard et al., *Clin. Pharmacol.,* (1993, Jan.), 35(5), 536P–537P.
F. Trigo–Rocha et al., *J. Urol.,* (1993, Apr.), 149, 872–877.
M. Krupp et al., *J. Cardiovas. Pharmacol.,* (1989), 13 (Supp. 2), S11–S19.
"Physicians' Desk Reference," (1992), 683,1099–1100, 1344, 1941–1943.
R. Morales et al., *World J. Urol.,* (1990), 8, 80–83.
J. Cortijo, *Br. J. Pharmacol.,* (1993, Feb.), 108(2), 562–568.
E. Kim et al., *J. Urol.,* (1995), 153, 361–365.
S. Korenman et al., *JAGS,* (1993, Apr.), 41(4), 363–366.
K. Allenby et al., *Angiology,* (1991), 42, 418–420.
H. Hamilton et al., *J. Med. Chem.,* (1987), 30, 91–96.
H. Padma–Nathan et al., *Sem. in Urol.,* (1986, Nov.), vol. IV, No. 4, 236–238.
J. Beavo et al., *TiPS,* (1990, Apr.), 11, 150–155.
S. Korenman et al., *Clin. Res.,* (1988), 36, 123A.
D. Halsted et al., *J. Urol.,* (1986, Jul.), 136, 109–110.
W. Thompson, *Pharmac. Ther.,* (1991), 51, 13–33.
M. Giembycz et al., *Clin. and Exper. Allergy,* (1992), 22, 337–344.
C. Nicholson et al., *TIPS,* (1991, Jan.), 12, 19–27.
J. LeBlanc et al., *Eur. J. Cardiothorac Surg.,* (1993), 7, 211–215.
C. Stief et al., *J. Urol.,* (1992, Nov.), 148, 1437–1440.
C. Stief et al., *World J. Urol.,* (1991), 9, 237–239.
C. Clyne et al., *Br. J. Surg.,* (1987, Apr.), 74, 246–248.
V. Mirone et al., *Acta. Urol. Ltd.,* (1992), Suppl. 4, 11–12.
P. Bush, Ph.D. Thesis (1992), pp. 159–160.
T. Lincoln, *Pharmac. Ther.,* (1989), 41, 479–502.
J. Heaton et al., *Urology,* (Feb. 1995), 45(2), 200–206.
A. Bowman et al., *Br. J. Pharmac.,* (1984), 81, 665–674.
F. Trigo–Rocha et al., *Am. J. Physiol.,* (1993, Feb.), 164, H419–H422.
J. Reiser et al., *Br. J. Dis. Chest,* (1986), 80, 157–163.
P. Bush et al., *J. Urol.,* (1992, Jun.), 147, 1650–1655.
F. Holmquist et al., *J. Urol.* (1993, Oct.), 150, 1310–1315.
R. Rudd et al., *Br. J. Dis. Chest,* (1983), 77, 78–86.
Beyer et al., *Phys. and Behav.,* (1981), 27, 731–733.
Pickard et al., *Br. J. Pharmacol.,* (1991), 104 755–759.
Martinez–Pineiro et al., *Eur. Urol.,* (1993), 24, 492–499.
Mirone et al., *Br. J. Urol.,* (Mar., 1993), 71(3), 365.
Murray et al., *Biochemical Soc. Trans.,* (1992), 20, 460–464.
Raeburn et al., *Prog. Drug. Res.,* (1993), 12–32.
Merkel, *Cardio Drug. Rev.,* (1993), 11(4), 501–515.
"Physicians' Desk Reference," (1992) 2207–2208.
Cimino et al., *Biochem. Pharmacology,* (1988), 37(14), 2739–2745.
Watanabe et al., *Federation Proceedings,* (1982), 41(7), 2292–2399.
Earl et al., *Life Sciences,* (1984), 35, 525–534.
Brindley, *Brit. J. Phychiat.,* (1983), 143, 332–337.
Keogh, *Aust. NZ. J. Med.,* (1989), 19, 108–112.
Funderbunk, *New Engl. J. Med.,* (1974), 290, 630–631.
Beretta, *Acta European Fertilitatis,* (1986), 17, 43–45.
"Physicians' Desk Reference," (1992), 1778–1779.
Hess in "Prazosin: Evaluation of a New Antihypertensive Agent," D. Cotton ed., American Elsevier, NY, (1974), 3–15.
Dadkar et al., *Ind. J. Exp. Biol.,* (1982), 20, 484–487.
D'Armiento et al., *Eur. J. Pharmacol.,* (1980), 65, 234–247.
Bhalla et al., *Brit. Med. J.,* (1979), 2, 1059.
Burke et al., *Med. J. Aust.,* (1980), 382–383.
Segasouthy et al., *Med. J. Malaysia,* (1982), 37(4), 384.
Ylitalo et al., *Acta Med. Scand.,* (1983), 213, 319–320.
Robbins et al., *J. Urol.,* (1983), 130, 975.
Adams et al., *J. Urol.,* (1984), 132, 1208.
Russell et al., *Med. J. Aust.,* (1985), 143, 321.
Taher et al., *Int. J. Impotence Res., Abstracts,* Milan, Italy (Sep. 14–17, 1992).
Saxena et al., *Journal of Medicinal Chemistry,* vol. 16, No. 5, 560–564 (1973).
Ishida et al., *Chem. Pharm. Bull.,* vol. 33, No. 8, 3237–3249 (1985).
Gillespie et al., *Molecular Pharmacology,* 36:773–781 (1989).
Braña et al., *Synthetic Communications,* 20(12), 1793–1820 (1990).
Dellouve–Courillon et al., *Tetrahedron,* 46, No. 9, 3245–3266 (1990).
Murray, *DN&P 6(3),* 150–156 (1993).
Zorgniotti et al. *Int. J. Impotence Res.,* 6, 33–36 (1994).

CYCLIC GMP-SPECIFIC PHOSPHODIESTERASE INHIBITORS

This invention relates to a series of tetracyclic derivatives, to processes for their preparation, pharmaceutical compositions containing them, and their use as therapeutic agents. In particular, the invention relates to tetracyclic derivatives which are potent and selective inhibitors of cyclic guanosine 3',5'-monophosphate specific phosphodiesterase (cGMP specific PDE) having utility in a variety of therapeutic areas where such inhibition is thought to be beneficial, including the treatment of cardiovascular disorders.

Thus, according to a first aspect, the present invention provides compounds of formula (I)

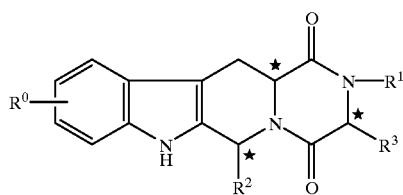

(I)

and solvates (e.g. hydrates) thereof, in which:

$R^0$ represents hydrogen, halogen or $C_{1-6}$ alkyl;

$R^1$ represents hydrogen or $C_{1-6}$alkyl;

$R^2$ represents the bicyclic ring

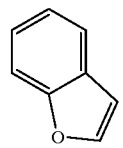

which may be optionally substituted by one or more groups selected from halogen and $C_{1-3}$alkyl; and $R^3$ represents hydrogen or $C_{1-3}$alkyl.

The term "halogen" as used herein denotes bromine, chlorine, fluorine and iodine.

The terms "$C_{1-3}$alkyl" and "$C_{1-6}$alkyl" as used herein denote a straight or branched alkyl chain such as methyl, ethyl, i-propyl, n-butyl, pentyl,hexyl or the like.

A particularly preferred subgroup of compounds according to the present invention are.compounds wherein $R^0$ represents hydrogen.

A further preferred subgroup includes compounds wherein $R^1$ is selected from hydrogen, methyl and isopropyl.

Preferably, $R^2$ represents the unsubstituted bicyclic ring

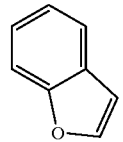

A still further subgroup of compounds of formula (I), are compounds wherein $R^3$ represents hydrogen or methyl.

It is to be understood that the present invention covers all appropriate combinations of particular and preferred groupings hereinabove.

The compounds of formula (I) may contain one or more asymmetric centres and thus can exist as enantiomers or diastereoisomers. It is to be understood that the invention includes both mixtures and separate individual isomers of the compounds of formula (I). Particularly preferred are 6R and 12aR isomers.

Particular individual compounds of the invention include:

(6R,12aR)-2,3,6,7,12,12a-Hexahydro-6-(5-benzofuranyl)-2-methyl-pyrazino[2',1':6,1]pyrido[3,4-b]indole-1,4-dione;

(6R,12aR)-2,3,6,7,12,12a-Hexahydro-6-(5-benzofuranyl)-pyrazino[2',1':6,1]pyrido[3,4-b]indole-1,4-dione;

(3S,6R,12aR)-2,3,6,7,12,12a-Hexahydro-6-(5-benzofuranyl)-3-methyl-pyrazino[2',1':6,1]pyrido[3,4-b]indole-1,4-dione;

(3S,6R,12aR)-2,3,6,7,12,12a-Hexahydro-6-(5-benzofuranyl)-2,3-dimethyl-pyrazino[2',1':6,1]pyrido[3,4-b]indole-1,4-dione;

(6R,12aR)-2,3,6,7,12,12a-Hexahydro-6-(5-benzofuranyl)-2-isopropyl-pyrazino[2',1':6,1]pyrido[3,4-b]indole-1,4-dione;

and physiologically acceptable solvates (e.g. hydrates) thereof.

A most particular compound of the invention is (6R,12aR)-2,3,6,7,12,12a-Hexahydro-6-(5-benzofuranyl)-2-methyl-pyrazino[2',1':6,1]pyrido[3,4-b]indole-1,4-dione;

and physiologically acceptable solvates (e.g. hydrates) thereof.

It has been shown that compounds of the present invention are potent and selective inhibitors of cGMP specific PDE. Thus, compounds of formula (I) are of interest for use in therapy, specifically for the treatment of a variety of conditions where inhibition of cGMP specific PDE is thought to be beneficial.

As a consequence of the selective PDE 5 inhibition exhibited by compounds of the present invention, cGMP levels are elevated, which in turn can give rise to beneficial anti-platelet, anti-neutrophil, anti-vasospastic, vasodilatory, natriuretic and diuretic activities as well as potentiation of the effects of endothelium-derived relaxing factor (EDRF), nitrovasodilators, atrial natriuretic factor (ANF), brain natriuretic peptide (BNP), C-type natriuretic peptide (CNP) and endothelium-dependent relaxing agents such as bradykinin, acetylcholine and 5-$HT_1$. The compounds of formula (I) therefore have utility in the treatment of a number of disorders, including stable, unstable and variant (Prinzmetal) angina, hypertension, pulmonary hypertension, congestive heart failure, renal failure, atherosclerosis, conditions of reduced blood vessel patency (e.g. post-percutaneous transluminal coronary angioplasty), peripheral vascular disease, vascular disorders such as Raynaud's disease, inflammatory diseases, stroke, bronchitis, chronic asthma, allergic asthma, allergic rhinitis, glaucoma, erectile dysfunction and diseases characterised by disorders of gut motility (e.g. irritable bowel syndrome).

It will be appreciated that references herein to treatment extend to prophylaxis as well as treatment of established conditions.

It will also be appreciated that 'a compound of formula (I),' or a physiologically acceptable salt or solvate thereof can be administered as the raw compound, or as a pharmaceutical composition containing either entity.

There is thus provided as a further aspect of the invention a compound of formula (I) for use in the treatment of stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma, erectile dysfunction or diseases characterised by disorders of gut motility (e.g. IBS).

According to another aspect of the invention, there is provided the use of a compound of formula (I) for the manufacture of a medicament for the treatment of stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma, erectile dysfunction or diseases characterised by disorders of gut motility (e.g. IBS).

In a further aspect, the invention provides a method of treating stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma, erectile dysfunction or diseases characterised by disorders of gut motility (e.g. IBS) in a human or non-human animal body which comprises administering to said body a therapeutically effective amount of a compound with formula (I).

Compounds of the invention may be administered by any suitable route, for example by oral, buccal, sub-lingual, rectal, vaginal, nasal, topical or parenteral (including intravenous, intramuscular, subcutaneous and intracoronary) administration. Oral administration is generally preferred.

For administration to man in the curative or prophylactic treatment of the disorders identified above, oral dosages of a compound of formula (I) will generally be in the range of from 0.5–800 mg daily for an average adult patient (70 kg). Thus for a typical adult patient, individual tablets or capsules contain from 0.2–400 mg of active compound, in a suitable pharmaceutically acceptable vehicle or carrier, for administration in single or multiple doses, once or several times per day. Dosages for intravenous, buccal or sublingual administration will typically be within the range of from 0.1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, a compound of the formula (I) can be administered alone, but will generally be administered in admixture with a pharmaceutical carrier selected with regard to the intended route of administration and standard pharmaceutical practice. For example, the compound may be administered orally, buccally or sublingually, in the form of tablets containing excipients such as starch or lactose, or in capsules or ovules either alone or in admixture with excipients, or in the form of elixirs or suspensions containing flavouring or colouring agents. Such liquid preparations may be prepared with pharmaceutically acceptable additives such as suspending agents (e.g. methylcellulose, a semi-synthetic glyceride such as witepsol or mixtures of glycerides such as a mixture of apricot kernel oil and PEG-6 esters or mixtures of PEG-8 and caprylic/capric glycerides). A compound may also be injected parenterally, for example intravenously, intramuscularly, subcutaneously or intracoronarily. For parenteral administration, the compound is best used in the form of a sterile aqueous solution which may contain other substances, for example salts, or monosaccharides such as mannitol or glucose, to make the solution isotonic with blood.

Thus, the invention provides in a further aspect a pharmaceutical composition comprising a compound of the formula (I) together with a pharmaceutically acceptable diluent or carrier therefor.

There is further provided by the present invention a process of preparing a pharmaceutical composition comprising a compound of formula (I), which process comprises mixing a compound of formula (I) together with a pharmaceutically acceptable diluent or carrier therefor.

A compound of formula (I) may also be used in combination with other therapeutic agents which may be useful in the treatment of the above-mentioned disease states. The invention thus provides, in another aspect, a combination of a compound of formula (I) together with another therapeutically active agent.

The combination referred to above may conveniently be presented for use in the form of a pharmaceutical formulation and thus pharmaceutical compositions comprising a combination as defined above together with a pharmaceutically acceptable diluent or carrier comprise a further aspect of the invention.

The individual components of such a combination may also be administered either sequentially or simultaneously in separate pharmaceutical formulations.

Appropriate doses of known therapeutic agents for use in combination with a compound of formula (I) will be readily appreciated by those skilled in the art.

Compounds of formula (I) may be prepared by any suitable method known in the art or by the following processes which form part of the present invention. In the methods below $R^0$, $R^1$, $R^2$ and $R^3$ are as defined in formula (I) above unless otherwise indicated.

Thus, a first process (A) for preparing a compound of formula (I) comprises treating a compound of formula (II)

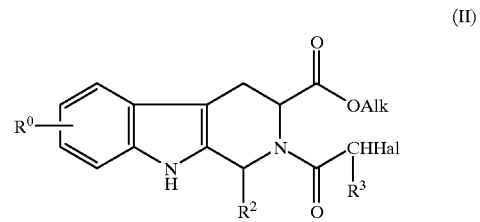

(II)

(in which Alk represents $C_{1-6}$alkyl, e.g. methyl or ethyl, and Hal is a halogen atom, e.g. chlorine) with a primary amine $R^1NH_2$ in a suitable solvent such as an alcohol (e.g. methanol or ethanol) or a mixture of solvents, conveniently at a temperature of from 20° C. to reflux (e.g. at about 50° C.).

According to a second process (B) for preparing a compound of formula (I) comprises hydrogenating a compound of formula (III)

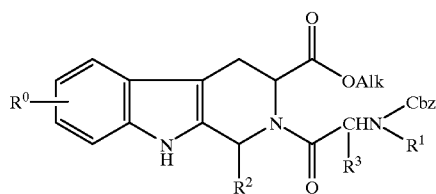

(III)

in which Alk is defined as above and Cbz represents a carbobenzyloxy group, in the presence of a catalyst e.g. palladium on activated carbon in a suitable solvent such as an alcohol, e.g. methanol or ethanol, at elevated temperature.

A compound of formula (II) may conveniently be prepared by treating a compound of formula (IV)

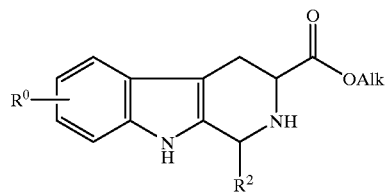

(IV)

with a haloacetyl halide (e.g. chloroacetyl chloride) in a suitable solvent such as a halogenated hydrocarbon (e.g. trichloromethane or dichloromethane), or an ether (e.g. tetrahydrofuran), preferably in the presence of a base such as an organic amine (e.g. a trialkylamine such as triethylamine) or an alkali metal carbonate or bicarbonate (e.g. NaHCO₃). The reaction may conveniently be effected at a temperature of from −20° C. to +20° C. (e.g. at about 0° C.).

A compound of formula (IV) may conveniently be prepared from a tryptophan alkyl ester of formula (V)

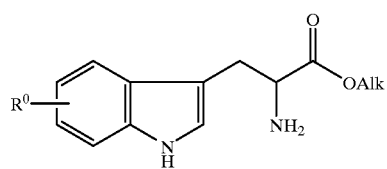

(V)

This step comprises a Pictet-Spengler cyclisation between a compound of formula (V) and an aldehyde R²CHO. The reaction may conveniently be effected in a suitable solvent such as a halogenated hydrocarbon (e.g. dichloromethane) or an aromatic hydrocarbon (e.g. toluene) in the presence of an acid such as trifluoroacetic acid. The reaction may conveniently be carried out at a temperature of from −20° C. to reflux to provide a compound of formula (III) in one step. The reaction may also be carried out in a solvent such as an aromatic hydrocarbon (e.g. benzene or toluene) under reflux, optionally using a Dean-Stark apparatus to trap the water produced. The reaction provides a mixture of cis and trans isomers which may be either individual enantiomers or racemates of pairs of cis or trans isomers depending upon whether racemic or enantiomerically pure tryptophan alkyl ester was used as the starting material. Individual cis or trans enantiomers may conveniently be separated from mixtures thereof by fractional crystallisation or by chromatography (e.g. flash column chromatography) using appropriate solvents and eluents. Similarly, pairs of cis and trans isomers may be separated by chromatography (e.g. flash column chromatography) using appropriate eluents. An optically pure trans isomer may also be converted to an optically pure cis isomer using suitable epimerisation procedures. One such procedure comprises treating the trans isomer or a mixture (e.g. 1:1 mixture) of cis and trans isomers with methanolic or aqueous hydrogen chloride at a temperature of from 0° C. to the refluxing temperature of the solution. The mixture is then subjected to chromatography (e.g. flash column chromatography) to separate the resulting diastereoisomers.

A compound of formula (III) may be prepared by reaction of a compound of formula (IV) as hereinbefore described, with a compound of formula (VI)

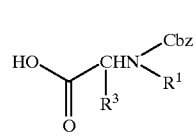

(VI)

wherein Cbz is defined above. Suitably, the reaction is carried out in the presence of 1,3-dicyclohexyl carbodiimide (DCC), in a solvent such as halogenated hydrocarbon (e.g. dichloromethane) from 0° C. to room temperature.

Compounds of formula (V) and (VI) are known compounds or may be prepared by standard methods hereinafter described.

Compounds of the invention may be isolated in association with solvent molecules by crystallisation from or evaporation of an appropriate solvent.

Thus, according to a further aspect of the invention, we provide a process (C) for preparing a compound of formula (I) or a solvate (e.g. hydrate) thereof which comprises process (A) or (B) as hereinbefore described followed by
  i) an interconversion step; and/or either
  ii) solvate (e.g. hydrate) formation.

The synthesis of the compounds of the invention and of the intermediates for use therein are illustrated by the following, non-limiting Examples.

Intermediates 1 and 2

(1R,3R)-Methyl 1,2,3,4-tetrahydro-1-(5-benzofuranyl)-9H-pyrido[3,4-b]indole-3-carboxylate, cis isomer and (1S,3R)-methyl 1,2,3,4-tetrahydro-1-(5-benzofuranyl)-9H-pyrido[3,4-b] indole-3-carboxylate trans isomer To a stirred solution of D-tryptophan methyl ester (3.73 g) and 5-formyl-benzofuran[1] (2.5 g) in anhydrous dichloromethane (1 00 mL) cooled at 0° C. was added dropwise trifluoroacetic acid (2.63 mL) and the solution was allowed to react at ambient temperature. After 72 hours, the solution was washed with a saturated aqueous solution of NaHCO₃, then with water and dried over Na₂SO₄.The organic layer was evaporated under reduced pressure and the residue was purified by flash chromatography eluting with dichloromethane/ethyl acetate (90/10) to give first the cis isomer (Intermediate 1) (3 g) as an amorphous compound, followed by the trans isomer (Intermediate 2) (2.5 g) as white crystals, m.p.: 194–195° C.

[1]The synthesis of 5-formyl-benzofuran is described in Chimie Thérapeutique 4, pp 221–227 (1966).

Intermediate 3

(1R,3R)-Methyl 1,2,3,4-tetrahydro-1-(5-benzofuranyl)-2-chloroacetyl-9H-pyrido[3,4-b] indole-3-carboxylate To a stirred solution of Intermediate 1 (2 g) and triethylamine (0.88 mL) in anhydrous dichloromethane (40 mL)

cooled at 0° C. was added dropwise chloroacetylchloride (0.5 mL) and the solution was stirred at the same temperature for 1 hour. The solution was washed with water, dried over $Na_2SO_4$ and evaporated to dryness and the residue was crystallised from methanol to give the title compound (1.8 g) as pale yellow crystals.

m.p.: 227–228° C.

Intermediate 4

(1R,3R)-Methyl 1,2,3,4-tetrahydro-1-(5-benzofuranyl)-2-(2-(S)-benzyloxycarbonylaminopropionyl)-9H-pyrido[3,4-b]indole-3-carboxylate To a stirred solution of (S)-2-benzyloxycarbonylaminopropionic acid (1.3 g) and 1,3-dicyclohexyl carbodiimide (DCC) (1.2 g) in anhydrous dichloromethane (50 ml) at 0° C. was added Intermediate 1 (1.0 g). The resulting mixture was stirred for 72 hours then the resulting precipitate filtered off. The filtrate was evaporated to dryness and the residue purified by flash chromatography, eluting with cyclohexane/ethyl acetate (60/40) to give the title compound as white crystals (1.4 g)

m.p.: 91–92° C.

Intermediate 5

(1R,3R)-Methyl 1,2,3,4-tetrahydro-1-(5-benzofuranyl)-2-[2-(S)-benzyloxycarbonylmethylamino)propionyl]-9H-pyrido[3,4-b]indole-3-carboxylate The same procedure as employed in the preparation of Intermediate 4 but starting from 2-(S)-benzyloxycarbonylmethylamino)propionic acid (0.82 g) and using Intermediate 1 (0.6 g), DCC (0.72 g) and dichloromethane (25 ml) gave after chromatography, eluting with cyclohexane/ethyl acetate (70/30), the title compound as a white foam.

$^1$H NMR (240 MHz, CDCl3) δ 7.7(s,1H), 7.6(d,2H), 7.4–7.05(m,11H), 6.6(d,1H), 5.4–5.0(m,4H), 3.5(d,1H), 3.0 (m,1H), 2.9–2.7(m,6H), 2.6(dd,1H), 1.3(s,3H).

EXAMPLE 1

(6R,12aR)-2,3,6,7,12,12a-Hexahydro-6-(5-benzofuranyl)-2-methyl-pyrazino[2',1':6,1]pyrido[3,4-b]indole-1,4-dione To a stirred suspension of Intermediate 3 (0.42 g) in methanol (30 mL) was added at ambient temperature a solution of methylamine (33% in EtOH) (0.47 mL) and the resulting mixture was heated at 50° C. under $N_2$ for 72 hours. The solvent was removed under reduced pressure and dissolved in dichloromethane. After washing with water, drying over $Na_2SO_4$ and evaporating to dryness, the crude product was purified by crystallisation from methanol to give the title compound as white crystals (0.21 g).

m.p.: 291–293° C.

Analysis for $C_{23}H_{19}N_3O_3$: Calculated: C, 71.68; H, 4.97; N, 10.90; Found: C, 71.5; H, 4.91; N, 10.74%.

$[\alpha]^{20}_D$=+55.7° (C=1; CHCl$_3$).

The Following Compounds were Obtained in a Similar Manner

EXAMPLE 2

(6R,12aR)-2,3,6,7,12,12a-Hexahydro-6-(5-benzofuranyl)-pyrazino[2',1':6,1]pyrido[3,4-]indole-1,4-dione The same procedure as employed in the preparation of Example 1 but starting from ammonia and Intermediate 3 gave, after recrystallisation from methanol, the title compound as white crystals.

m.p.: 310–311° C.

Analysis for $C_{22}H_{17}N_3O_3$ (0.4 MeOH): Calculated: C, 70.03; H, 4.88; N, 10.94; Found: C, 70.01; H, 4.8; N, 10.61%;

$[\alpha]^{20}_D$=+60.4° (C=0.5; pyridine).

EXAMPLE 3

(6R,12aR)-2,3,6,7,12,12a-Hexahydro-6-(5-benzofuranyl)-2-isopropyl-pyrazino[2',1':6,1]pyrido[3,4-b]indole-1,4-dione The same procedure as employed in the preparation of Example 1 but starting from isopropylamine and Intermediate 3 gave, after recrystallisation from methanol, the title compound as white crystals.

m.p.: 291–292° C.

Analysis for $C_{25}H_{23}N_3O_3$ (0.6 MeOH): Calculated: C, 71.06; H, 5.92; N, 9.71; Found: C, 70.94; H, 5.62; N, 9.77%.

$[\alpha]^{20}_D$=+37.9° (C=1; CHCl$_3$).

EXAMPLE 4

(3S,6R,12aR)-2,3,6,7,12,12a-Hexahydro-6-(5-benzofuranyl)-3-methyl-pyrazino[2',1':6,1]pyrido[3,4-b]indole-1,4-dione A solution of Intermediate 4 (0.3 g) in the presence of 10% Pd/C (30 mg) in methanol (10 ml) was stirred under an atmosphere of hydrogen at 50° C. for two hours. The reaction mixture was cooled, filtered through Celite, the filter cake washed with methanol and the filtrate evaporated in vacuo. The residue was purified by flash chromatography, eluting with dichloromethane/methanol (98/2) to give the title compound as white crystals after recrystallisation from methanol (0.15 g)

m.p.: 150–151° C.

Analysis for $C_{23}H_{19}N_3O_3$ (0.1 MeOH) Calculated: C, 71.39; H, 5.03; N, 10.81; Found: C, 71.08; H, 5.16; N, 10.50%;

$[\alpha]^{20}_D$=+50° (C=0.25; CHCl$_3$).

EXAMPLE 5

(3S,6R,12aR)-2,3,6,7,12,12a-Hexahydro-6-(5-benzofuranyl)-2,3-dimethyl-pyrazino[2',1':6,1]pyrido[3,4-b]indole-1,4-dione The same procedure as employed in in the preparation of Example 4 but starting from Intermediate 5 (0.52 g) and using 10% Pd/C (50 mg) in methanol (20 ml) gave, after recrystallisation from methanol, the title compound as white crystals (40 mg).

m.p.: 323–324° C.

Analysis for $C_{24}H_{21}N_3O_3$. (0.1 Methanol) Calculated: C, 71.52; H, 5.35; N, 10.43; Found: C, 71.71; H, 5.44; N, 10.39%;

$[\alpha]^{20}_D$=+53° (C=0.35; CHCl$_3$).

Tablets for Oral Administration

A. Direct Compression

| 1. | mg/tablet |
|---|---|
| Active ingredient | 50.0 |
| Crospovidone USNF | 8.0 |
| Magnesium Stearate Ph Eur | 1.0 |
| Anhydrous Lactose | 141.0 |

The active ingredient was sieved and blended with the excipients. The resultant mix was compressed into tablets.

| 2. | mg/tablet |
|---|---|
| Active ingredient | 50.0 |
| Colloidal Silicon Dioxide | 0.5 |
| Crospovidone | 8.0 |
| Sodium Lauryl Sulphate | 1.0 |
| Magnesium Stearate Ph Eur | 1.0 |
| Microcrystalline Cellulose USNF | 139.5 |

The active ingredient was sieved and blended with the excipients. The resultant mix was compressed into tablets.

B. Wet Granulation

| 1. | mg/tablet |
|---|---|
| Active ingredient | 50.0 |
| Polyvinyl pyrollidone | 150.0 |
| Polyethylene glycol | 50.0 |
| Polysorbate 80 | 10.0 |
| Magnesium Stearate Ph Eur | 2.5 |
| Croscarmellose Sodium | 25.0 |
| Colloidal Silicon Dioxide | 2.5 |
| Microcrystalline Cellulose USNF | 210.0 |

The polyvinyl pyrollidone, polyethylene glycol and polysorbate 80 were dissolved in water. The resultant solution was used to granulate the active ingredient. After drying the granules were screened, then extruded at elevated temperatures and pressures. The extrudate was milled and/or screened then was blended with the microcrystalline cellulose, croscarmellose sodium, colloidal silicon dioxide and magnesium stearate. The resultant mix was compressed into tablets.

| 2. | mg/tablet |
|---|---|
| Active ingredient | 50.0 |
| Polysorbate 80 | 3.0 |
| Lactose Ph Eur | 178.0 |
| Starch BP | 45.0 |
| Pregelatinised Maize Starch BP | 22.5 |
| Magnesium Stearate BP | 1.5 |

The active ingredient was sieved and blended with the lactose, starch and pregelatinised maize starch. The polysorbate 80 was dissolved in purified water. Suitable volumes of the polysorbate 80 solution were added and the powders were granulated. After drying, the granules were screened and blended with the magnesium stearate. The granules were then compressed into tablets.

Tablets of other strengths may be prepared by altering the ratio of active ingredient to the other excipients.

Film Coated Tablets

The aforementioned tablet formulations were film coated.

| Coating Suspension | % w/w |
|---|---|
| Opadry white† | 13.2 |
| Purified water Ph Eur | to 100.0* |

*The water did not appear in the final product. The maximum theoretical weight of solids applied during coating was 20 mg/tablet.
†Opadry white is a proprietary material obtainable from Colorcon Limited, UK which contains hydroxypropyl methylcellulose, titanium dioxide and triacetin.

The tablets were film coated using the coating suspension in conventional film coating equipment.

Capsules

| 1. | mg/capsule |
|---|---|
| Active ingredient | 50.0 |
| Lactose | 148.5 |
| Polyvinyl pyrollidone | 100.0 |
| Magnesium Stearate | 1.5 |

The active ingredient was sieved and blended with the excipients. The mix was filled into size No. 1 hard gelatin capsules using suitable equipment.

| 2. | mg/capsule |
|---|---|
| Active ingredient | 50.0 |
| Microcrystalline Cellulose | 233.5 |
| Sodium Lauryl Sulphate | 3.0 |
| Crospovidone | 12.0 |
| Magnesium Stearate | 1.5 |

The active ingredient was sieved and blended with the excipients. The mix was filled into size No. 1 hard gelatin capsules using suitable equipment.

Other doses may be prepared by altering the ratio of active ingredient to excipient, the fill weight and if necessary changing the capsule size.

| 3. | mg/capsule |
|---|---|
| Active ingredient | 50.0 |
| Labrafil M1944CS | to 1.0 ml |

The active ingredient was sieved and blended with the Labrafil. The suspension was filled into soft gelatin capsules using appropriate equipment.

Inhibitory Effect on cGMP-PDE cGMP-PDE activity of compounds of the present invention was measured using a one-step assay adapted from Wells at al. (Wells, J. N., Baird, C. E., Wu, Y. J. and Hardman, J. G., Biochim. Biophys. Acta 384, 430 (1975)). The reaction medium contained 50 mM Tris-HCl,pH 7.5, 5 mM Mg-acetate, 250 μg/ml 5'-Nucleotidase, 1 mM EGTA and 0.15 μM 8-[$H^3$]-cGMP. The enzyme used was a human recombinant PDE V (ICOS, Seattle U.S.A.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves using typically concentrations ranging from 10 nM to 10 μM. Tests against other PDE enzymes using standard methodology also showed that compounds of the invention are highly selective for the cGMP specific PDE enzyme.

cGMP Level Measurements

Rat aortic smooth muscle cells (RSMC) prepared according to Chamley et al. in Cell Tissue Res. 177, 503–522 (1977) were used between the 10th and 25th passage at confluence in 24-well culture dishes. Culture media was aspirated and replaced with PBS (0.5 ml) containing the compound tested at the appropriate concentration. After 30 minutes at 37° C., particulates guanylate cyclase was stimulated by addition of ANF (100 nM) for 10 minutes. At the end of incubation, the medium was withdrawn and two extractions were performed by addition of 65% ethanol (0.25 ml). The two ethanolic extracts were pooled and evaporated until dryness, using a Speed-vat system. c-GMP was measured after acetylation by scintillation proximity immunoassay (AMERSHAM). The $EC_{50}$ values are expressed as the dose giving half of the stimulation at saturating concentrations.

Biological Data

The compounds according to the present invention were typically found to exhibit an $IC_{50}$ value of less than 500 nM and an $EC_{50}$ value of less than 5 μM. In vitro test data for representative compounds of the invention is given in the following table:

TABLE 1

| In vitro results | | |
|---|---|---|
| Example No. | $IC_{50}$ nM | $EC_{50}$ μM |
| 1 | 15 | 0.6 |
| 2 | 20 | <1 |
| 3 | 30 | <1 |
| 4 | 8 | <1 |
| 5 | 8 | <1 |

The hypotensive effects of compounds according to the invention as identified in Table 2 were studied in conscious spontaneously hypertensive rats (SHRs). The compounds were administered orally at a dose of 5 mg/kg in a mixture of 5% DMF and 95% olive oil. Blood pressure was measured from a catheter inserted in the carotid artery and recorded for 5 hours after administration. The results are expressed as Area Under the Curve (AUC from 0 to 5 hours, mmHg.hour) of the fall in blood pressure over time.

TABLE 2

| In vivo results | |
|---|---|
| Example No. | AUC PO (mmHg · h) |
| 1 | 137 |
| 2 | 93 |
| 3 | 108 |
| 4 | 101 |
| 5 | 89 |

We claim:
1. A compound of formula (I)

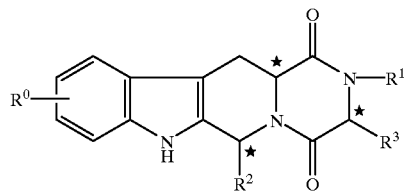

and solvates thereof, in which:

$R^0$ represents hydrogen, halogen or $C_{1-6}$ alkyl;
$R^1$ represents hydrogen or $C_{1-6}$ alkyl;
$R^2$ represents the bicyclic ring;

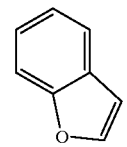

and
$R^3$ represents hydrogen or $C_{1-3}$ alkyl.

2. A compound according to claim 1 wherein $R^0$ represents hydrogen.

3. A compound according to claim 1 wherein $R^1$ is selected from hydrogen, methyl, and iso-propyl.

4. A compound according to claim 1 wherein $R^3$ represents hydrogen or methyl.

5. (6R,12aR)-2,3,6,7,12,12a-Hexahydro-6-(5-benzofuranyl)-2-methyl-pyrazino[2',1':6,1]pyrido[3,4-b]indole-1,4-dione;
(6R,12aR)-2,3,6,7,12,12a-Hexahydro-6-(5-benzofuranyl)-pyrazino[2',1':6,1]pyrido[3,4-b]indole-1,4-dione;
(3S,6R,12aR)-2,3,6,7,12,12a-Hexahydro-6-(5-benzofuranyl)-3-methyl-pyrazino[2',1':6,1]pyrido[3,4-b]indole-1,4-dione;
(3S,6R,12aR)-2,3,6,7,12,12a-Hexahydro-6-(5-benzofuranyl)-2,3-dimethyl-pyrazino[2',1':6,1]pyrido[3,4-b]indole-1,4-dione;
(6R,12aR)-2,3,6,7,12,12a-Hexahydro-6-(5-benzofuranyl)-2-isopropyl-pyrazino[2',1':6,1]pyrido[3,4-b]indole-1,4-dione;

and physiologically acceptable solvates thereof.

6. (6R,12aR)-2,3,6,7,12,1 2a-Hexahydro-6-(5-benzofuranyl)-2-methyl-pyrazino[2',1':6,1]pyrido[3,4-b]indole-1,4-dione.

7. A process for preparing a compound according to claim 1

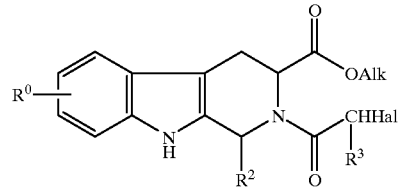

comprising hydrogenating a compound of formula (III)

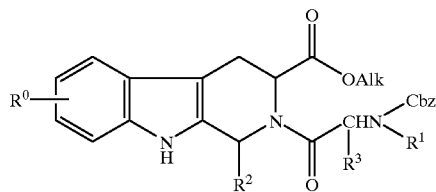

in which Alk is defined as above and Cbz represents a carbobenzyloxy group, in the presence of a catalyst in a suitable solvent such as an alcohol, at elevated temperature; optionally followed by i) an interconversion step; and/or iii) solvate formation.

8. A pharmaceutical composition comprising a compound according to claim 1, together with a pharmaceutically acceptable diluent or carrier therefor.

9. A process of preparing a pharmaceutical composition comprising a compound according to claim 1, which process comprises mixing said compound together with a pharmaceutically acceptable diluent or carrier therefor.

10. A method of treating conditions where inhibition of cGMP specific PDE is of therapeutic benefit, in a human or non-human animal body, which comprises administering to said body a therapeutically effective amount of a compound according to claim 1.

11. The method of claim 10 wherein the condition is erectile dysfunction.

12. The method of claim 11 wherein the animal body is human.

13. The method of claim 11 wherein the compound is administered orally.

* * * * *

UNITED STATES PATENT AND TRADEMARK OFFICE
CERTIFICATE OF CORRECTION

PATENT NO.     : 5,981,527
DATED          : November 9, 1999
INVENTOR(S)    : Daugan et al.

It is certified that error appears in the above-identified patent and that said Letters Patent is hereby corrected as shown below:

Title page,
Item [56], References Cited, OTHER PUBLICATIONS, "F. Trigo-Rocha et al." reference, "164" should be -- 264 --

Column 1,
Line 49, "are.compounds" should be -- are compounds --

Column 6,
Line 49, "(1 00 mL)" should be -- (100 mL) --

Column 7,
Lines 59-60, "The Following Compounds were Obtained in a similar Manner" should be -- The following compounds were obtained in a similar manner: --

Column 11,
Line 19, "Speed-vat system." should be -- Speed-vac system. --

Column 12,
Line 54, "dione." should be -- dione; and physiologically acceptable solvates thereof. --

Column 13,
Lines 15-19, "followed by i) an interconversion step; and/or iii) solvate formation." should be -- followed by: i) an interconversion step; and/or ii) solvate formation. --

Signed and Sealed this

Ninth Day of March, 2004

JON W. DUDAS
*Acting Director of the United States Patent and Trademark Office*